(12) United States Patent
Nan

(10) Patent No.: US 6,579,229 B1
(45) Date of Patent: Jun. 17, 2003

(54) ELASTIC HARNESS FOR HOLDING A PROSTHESIS AID

(75) Inventor: Simon Siu Man Nan, Hong Kong (HK)

(73) Assignee: Nanma Ltd., Mauritius ( * ) Notice: Subject to any disclaimer, the term of this patent is extended or adjusted under 35 U.S.C. 154(b) by 0 days.

(21) Appl. No.: 10/134,934

(22) Filed: Apr. 29, 2002

(51) Int. Cl.$^7$ .................................................. A61F 5/00
(52) U.S. Cl. ........................................................ 600/38
(58) Field of Search ..................................... 600/38–41

(56) References Cited

U.S. PATENT DOCUMENTS

| | | | | |
|---|---|---|---|---|
| 4,429,689 A | * | 2/1984 | Yanong | 600/39 |
| 4,488,541 A | * | 12/1984 | Garcia | 600/39 |
| 4,643,175 A | * | 2/1987 | Chapman | 600/38 |
| 5,127,396 A | | 7/1992 | McAllister | |
| 5,893,827 A | * | 4/1999 | Jaquez et al. | 600/38 |
| 5,911,686 A | | 6/1999 | Kohut | |
| 6,036,635 A | | 3/2000 | Altshuler | |
| 6,193,753 B1 | | 2/2001 | Nordheim et al. | |
| 6,251,067 B1 | | 6/2001 | Strickholm | |
| 6,346,492 B1 | | 2/2002 | Koyfman | |

OTHER PUBLICATIONS

Good Vibrations Catalog, pp. 22, 23 and 28–31, Dec. 1997.*

* cited by examiner

*Primary Examiner*—Samuel G. Gilbert
(74) *Attorney, Agent, or Firm*—Greensfelder, Hemker & Gale, P.C.

(57) ABSTRACT

An elastic harness for supporting a prosthesis aid is disclosed comprising an arrangement of beads and clamps used to configure elastic tubing into a harness shape adapted to comfortably fit around the lower body.

26 Claims, 4 Drawing Sheets

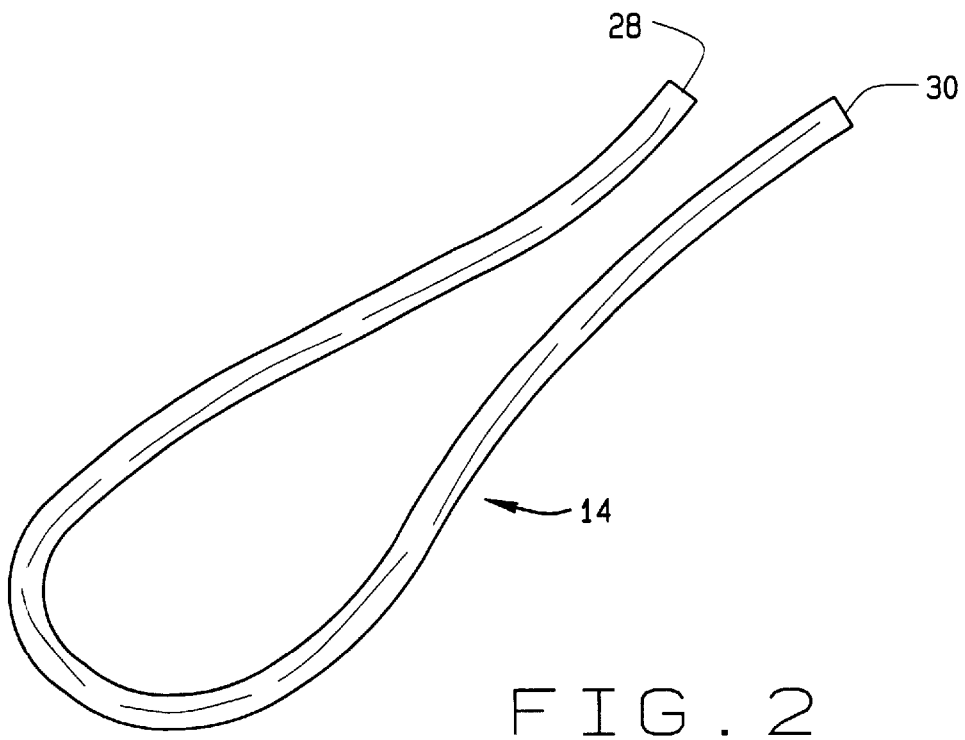
FIG. 2
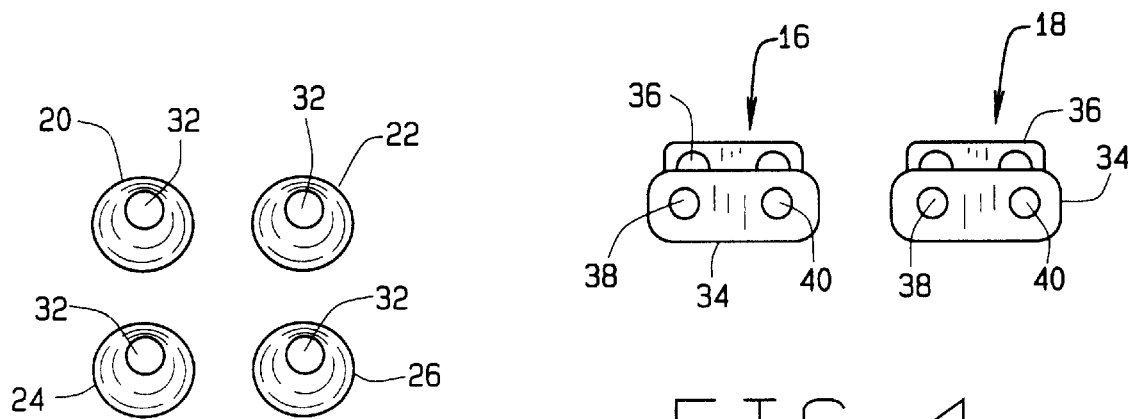
FIG. 3
FIG. 4

ELASTIC HARNESS FOR HOLDING A PROSTHESIS AID

BACKGROUND OF THE INVENTION

1. Field of the Invention

The present invention relates to a device for supporting a prosthesis aid, and more particularly to an elastic harness for supporting such an aid. More specifically, the present invention relates an elastic harness that is easy to assemble and adjust.

2. Prior Art

Many human males suffer from erectile dysfunction for a variety of reasons. In the United States alone, an estimated 10% of the male population suffers from erectile dysfunction. Devices, such as phallic prosthesis aids, are designed to simulate sexual intercourse for men suffering from erectile dysfunction. For example, U.S. Pat. No. 6,251,067 to Strickholm discloses a male erectile prosthesis that can be utilized to allow a man with erectile dysfunction to participate in sexual activity. The erectile prosthesis of Strickholm comprises a penile wrap attached to a plate element that is designed to fit against the pelvic region of a user and support the prosthesis device in combination with the penile wrap.

U.S. Pat. No. 5,127,396 to McAllister discloses a prosthetic device having a plug supported by an adjustable harness formed of an inelastic cloth-like material that wraps around the user's lower abdomen, between the legs, and up onto or over the user's buttocks.

Although the above prosthetic devices disclose adequate means of supporting a prosthesis aid onto a user's body, further improvements in the art are desirable. For example, prior art harnesses are typically made from an inelastic material, such as cloth or leather, that may be difficult to adjust and can fit too constrictively around the user's lower body if improperly adjusted. Further, many harnesses require a thrust plate or similar plate element to properly support the prosthesis aid which adds to the overall expense of manufacturing the prosthetic device.

Therefore, there appears a need in the art for a prosthetic device that has an elastic harness for supporting a prosthesis aid that is easily adjustable and fits comfortably around the user's lower body. There also appears a need in the art for a harness that is of simple construction and may be inexpensively manufactured.

OBJECTS AND SUMMARY OF THE INVENTION

Accordingly, the primary feature of the present invention is to provide a means for wearing a prosthesis aid.

Another feature of the present invention is to provide an elastic harness for supporting a prosthesis aid in order to conduct simulated sexual activity.

A further feature of the present invention is to provide a method for assembling an elastic harness that requires no sewing.

Another further feature of the present invention is to provide an elastic harness that may used to securely support a phallic prosthesis aid.

Yet another object of the present invention is to provide an elastic harness that is easily adjustable and fits comfortably around the person's lower body.

A further object of the present invention is to provide a harness that may be quickly assembled and disassembled by the user.

These and other objects of the present invention are realized in the preferred embodiment of the present invention, described by way of example and not by way of limitation, which provides for an elastic harness for supporting a prosthesis aid.

In brief summary, the present invention overcomes and substantially alleviates the deficiencies in the prior art by providing an elastic harness for supporting a prosthesis aid. The harness of the present invention comprises an elastic tubing assembled using an arrangement of beads having apertures and spring clamps that configure the tubing into a harness shape adapted to fit around the user's lower body and support a prosthesis aid. Specifically, the above arrangement includes first, second, third and fourth beads used with first and second spring clamps to configure the elastic tubing into first and second lower segments attached to an upper segment with a portion of the elastic tubing meets in coincidental alignment to define an inguinal portion. The inguinal portion includes, upper and lower adjustment segments for properly adjusting the harness around the user and a supporting segment for supporting the prosthesis aid. This arrangement configures the harness to permit the prosthesis aid to be securely supported at its proximal end while allowing for convenient adjustment of the harness around the user's lower body.

According to one aspect of the present invention, the method of assembling the harness comprises the steps of providing an elastic tubing with opposite free ends, first, second, third and fourth beads and first and second spring clamps as described above. To assemble, the user first makes a loop with the tubing by inserting one free end of tubing through the aperture of the first bead and then re-inserting the same free end through the other end of the aperture such that a loop is formed. The user repeats this procedure for the second, third and fourth beads by inserting both free ends through the same aperture of each respective bead. Once the procedure has been repeated with all the beads, the user inserts one of the free ends through a first hole of one of the spring clamps, and then through the eye of the loop made by the tubing. Once so inserted, the user threads the same free end of tubing through the second hole of the spring clamp which creates a loop from the tubing that engages the upper segment of the harness formed by the first loop. The user then repeats this procedure with the other free end so that the harness of the present invention is fully assembled.

Additional objects, advantages and novel features of the invention will be set forth in the description which follows, and will become apparent to those skilled in the art upon examination of the following more detailed description and drawings in which like elements of the invention are similarly numbered throughout.

BRIEF DESCRIPTION OF THE DRAWINGS

FIG. 2 is a perspective view of tubing used to configure the harness according to the present invention;

FIG. 3 is a perspective view of four beads used to assemble the harness according to the present invention;

FIG. 4 is a perspective view of two clamps used to assemble the harness according to the present invention;

DETAILED DESCRIPTION OF THE INVENTION

Figure 1:
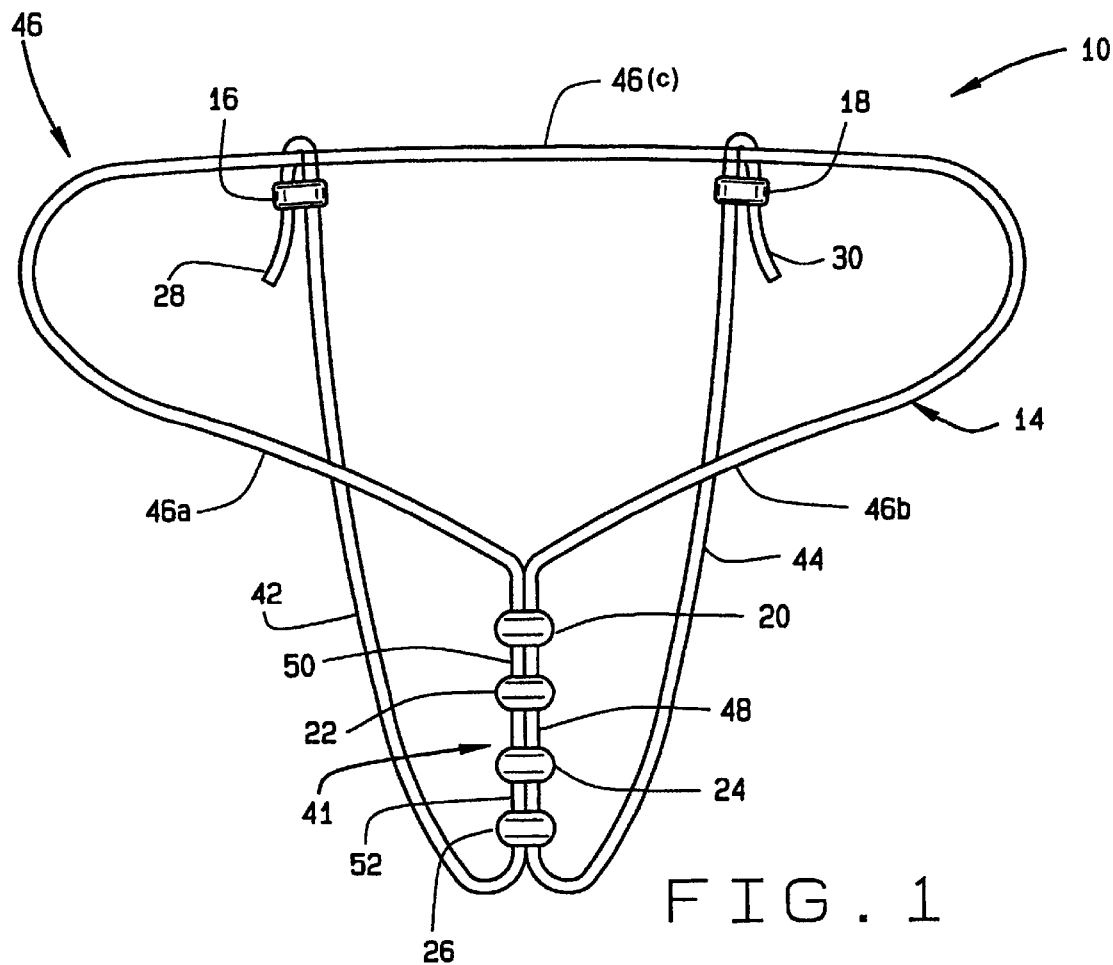
FIG. 1 is a perspective view of a harness according to the present invention.

Referring to the drawings, the preferred embodiment of the harness of the present invention is illustrated and generally indicated as 10 in FIG. 1. Harness 10 provides a means for securely supporting a prosthesis aid 12 (FIG. 9) on a user in order to simulate sexual activity. Referring to FIGS. 1 and 2, harness 10 comprises an elongated elastic tubing 14 having free ends 28 and 30 which is assembled into a particular harness-shaped arrangement illustrated specifically in FIG. 1. To assist in assembly, harness 10 is provided with spring clamps 16 and 18 as well as first, second, third and fourth hollow beads 20, 22, 24 and 26 to assemble harness 10 as shall be discussed in greater detail below.

Referring to FIG. 3, first, second, third, and fourth beads 20, 22, 24 and 26 are conventional spherical-shaped beads with an aperture 32 formed through the body of each bead. Apertures 32 are sized and shaped to receive elastic tubing 14 therethrough when configuring harness 10. As shown in FIG. 4, spring clamps 16 and 18 are also provided as a means for configuring tubing 14 and engaging free ends 28 and 30 thereof to form respective loops around another portion of tubing 14 during assembly of harness 10. Each spring clamp 16 and 18 is of conventional construction and includes a two-part body 34 having first and second openings 38 and 40 formed therethrough which are sized and shaped to receive elastic tubing 14. As further shown, body 34 includes a biased clip member 36 that is adapted to securely engage elastic tubing 14 when tubing 14 is inserted through either first or second opening 38 or 40. Normally, clip member 34 is in a biased closed position; however, when the user pushes down against member 34, member 34 is placed in an open position and the elastic tubing 14 may be inserted through either first or second opening 38 or 40. When clip member 34 is released to its normally closed and biased position member 34 securely engages elastic tubing 14.

When fully assembled, harness 10 comprises an arrangement of first, second, third and fourth beads 20, 22, 24 and 26 used with spring clamps 16 and 18 first to configure the elastic tubing 14 into first and second lower segments 42 and 44. The free ends 28 and 30 of first and second lower segments 42 and 44, respectively, are secured to an upper segment 46 of harness 10 formed by elastic tubing 14. Upper segment 46 of elastic tubing 14 forms an upper posterior segment 46c which fits around the posterior portion of a person's waist above the buttocks while upper anterior segments 46a and 46b, respectively, fit around the anterior portions of a person's waist. Upper anterior segments 46a and 46b meet in coincidental alignment to form an inguinal portion 41. As further shown, inguinal portion 41 comprises a supporting segment 48 which is interposed between upper and lower adjustment segments 50 and 52. This particular arrangement permits the proximal end of the prosthesis aid 12 to be securely supported between the inguinal portion 41 of elastic tubing 14 forming supporting segment 48 of harness 10 between second and third beads 22 and 24, respectively. This arrangement also allows for easy adjustment of the harness 10 around the user's lower body utilizing first and fourth beads, 20 and 26, respectively, to properly adjust the upper and lower adjustment segments 50 and 52 of harness 10 around the person's waist and inguinal regions.

Figure 5:
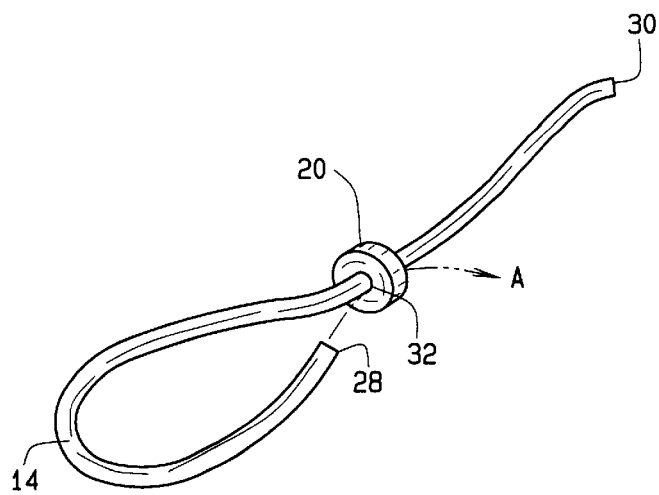
FIG. 5 is a perspective view of tubing and one of the beads illustrating the method of forming one of the loop ends according to the present invention.

Referring to FIGS. 5–8, the method for assembling the harness 10 of the present invention will be discussed. As illustrated in FIG. 5, the user first inserts free end 28 of elastic tubing 14 through aperture 32 of first bead 20 in one direction and then reinserts the same end 28 again through aperture 32 in direction A in order to form a loop A (FIG. 6) that defines upper segment 46 of harness 10. After loop A has been formed, the user inserts free end 30 of elastic tubing 14 through the aperture 32 of second bead 22 and then similarly inserts free end 28 through the same aperture 32 such that upper adjustment segment 50 is formed. This procedure is repeated for third and fourth beads 24 and 26 until supporting segment 48 and lower adjustment segment 52 of harness 10 are also formed.

Figure 8:
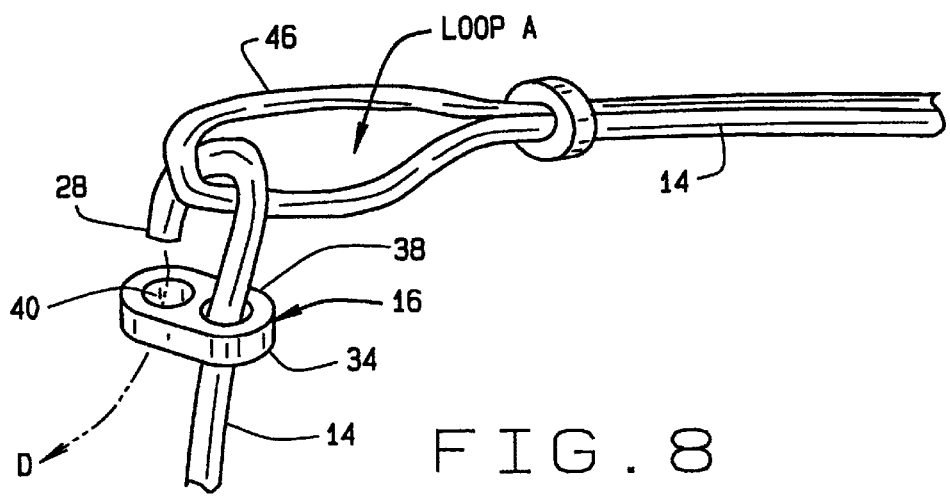
FIG. 8 is a perspective view illustrating the method of engaging the free end of tubing with one of the spring clamps to form a loop according to the present invention.
Figure 6:
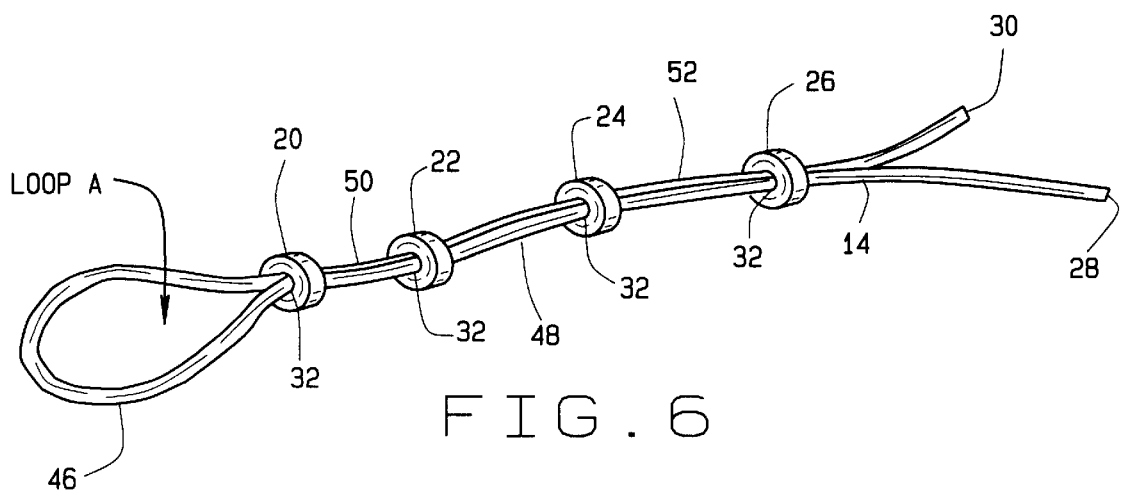
FIG. 6 is a perspective view of the tubing and all four beads illustrating the method of forming the upper and lower adjustment segments and support segment of the harness according to the present invention.
Figure 7:
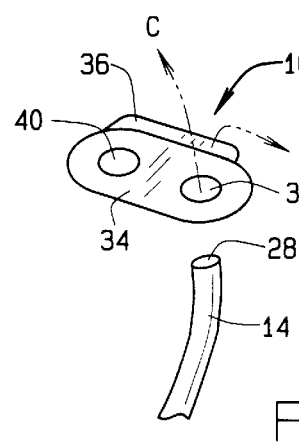
FIG. 7 is a perspective view illustrating the method of engaging the free end of tubing with one of the spring clamps according to the present invention.

Once first, second, third and fourth beads 20, 22, 24 and 26 are properly engaged to elastic tubing 14 as illustrated in FIG. 6, the user inserts free end 28 of elastic tubing 14 through first opening 38 of spring clamp 16 in direction C by first depressing the clip member 36 thereof in direction B. As the clip member 36 is depressed, the user may insert free end 28 through both first opening 38 and loop A as illustrated in FIG. 8. Once the free the free end 28 is threaded through loop A the user then inserts end 28 through second opening 40 of spring clamp 16 in direction D such that end 28 forms a loop with clamp 16 that engages loop A of upper segment 46. This procedure is repeated for free end 30 and spring clamp 18 so that end 30 is formed into a similar loop with clamp 18 that engages loop A of upper segment 46.

Figure 9:
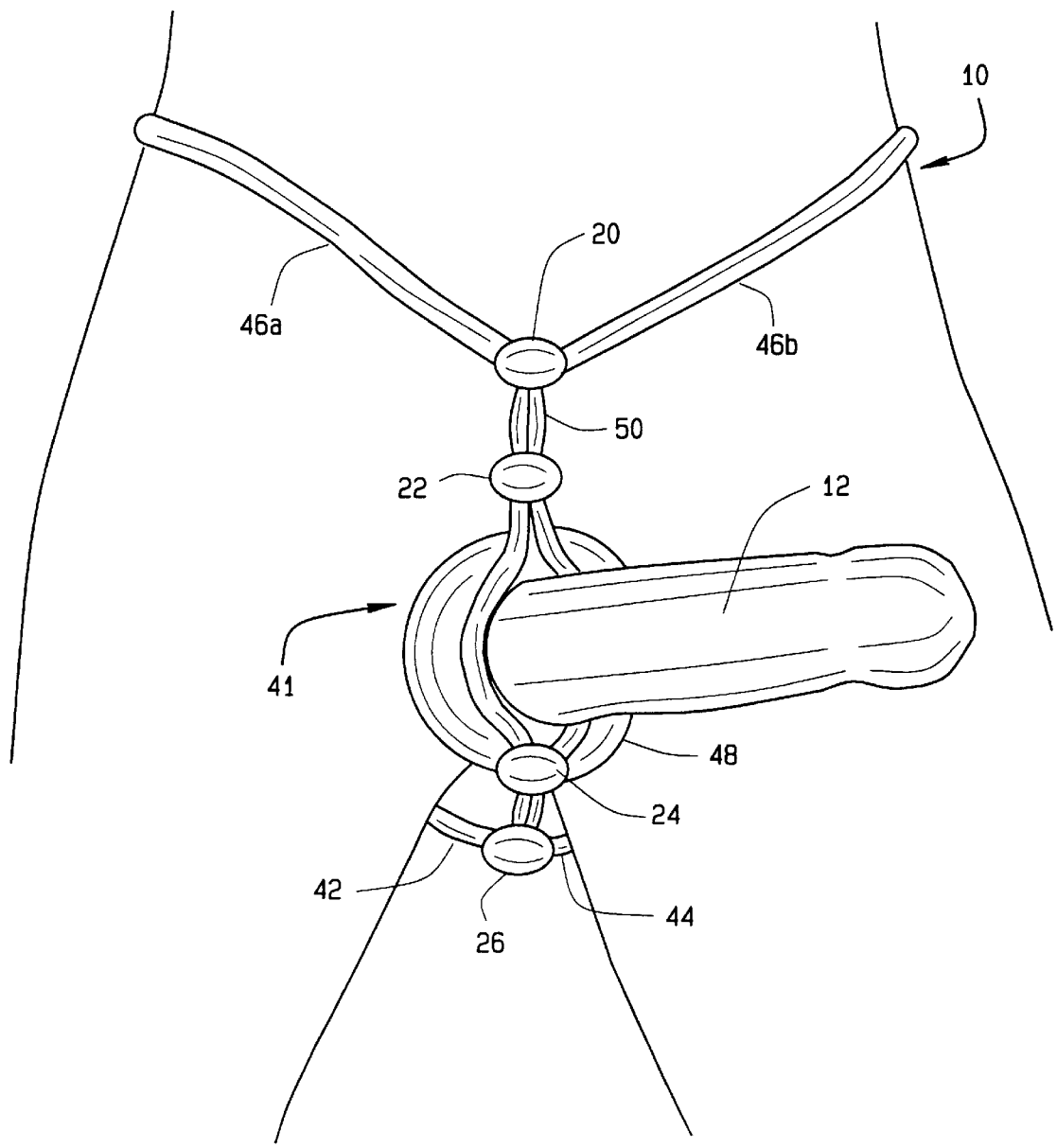
FIG. 9 is a perspective view of the harness supporting a prosthesis aid being worn by a user according to the present invention.

After harness 10 has been fully assembled, the user inserts one of his legs between upper segment 46 and first lower segment 42, while inserting the other leg between supporting segment 48 and second lower segment 44 as illustrated in FIG. 9. The user may then adjust harness 10 by moving first bead 20 to adjust the supporting segment 48 around the user's waist, while moving fourth bead 26 to adjust the depth of first and second lower segments 42 and 44.

Preferably, elastic tubing 14 is made from a flexible plastic material; however any material exhibiting suitable elasticity or flexibility which is sized and shaped to be threaded through first, second, third and fourth beads 20, 22, 24 and 26 as well as spring clamps 16 and 18 is felt to fall within the scope of the present invention. Further, first, second, third and fourth beads 20, 22, 24 and 26 are ordinary hollow beads, while first and second spring cl amps 16 and 18 are conventional spring clamps.

It should be understood from the foregoing that, while particular embodiments of the invention have been illustrated and described, various modifications can be made thereto without departing from the spirit and scope of the invention. Therefore, it is not intended that the invention be limited by the specification; instead, the scope of the present invention is intended to be limited only by the appended claims.

What is claimed is:

1. A support for a prosthesis device comprising:
   a harness made of an elastic tubing configured to fit around a body using a plurality of beads and clamps, said tubing configured to form first and second lower segments connected to an upper segment adapted to fit around a waist of the body by said clamps, said upper segment of said tubing meeting in coincidental alignment along one section thereof and attached together by said plurality of beads to define an inguinal portion, said inguinal portion defining a support segment formed between any two of said plurality of beads, wherein said support segment is adapted to securely support a portion of the prosthesis device.

2. The support according to claim 1, wherein said plurality of beads comprises first, second, third and fourth beads.

3. The support according to claim 2, wherein said inguinal portion further defines an upper adjustment segment of a pre-determined length and a lower adjustment segment of a pre-determined length.

4. The support according to claim 3, wherein said upper adjustment segment is formed between said first and second beads.

5. The support according to claim 3, wherein said lower adjustment segment is formed between said third and fourth beads.

6. The support according to claim 3, wherein adjustment of said upper adjustment segment changes the pre-determined length of said upper segment.

7. The support according to claim 3, wherein adjustment of said lower adjustment segment changes the pre-determined length of said tubing between said first and second lower segments.

8. The support according to claim 1, wherein said inguinal portion comprises first, second, third and fourth beads arranged along said tubing.

9. The support according to claim 8, wherein said tubing between said second and third beads support said prosthesis device.

10. The support according to claim 8, wherein movement of said first bead adjusts the length of said upper segment.

11. The support according to claim 8, wherein movement of said fourth bead adjusts the length of said first and second lower segment.

12. The support according to claim 1, wherein said upper segment includes an upper posterior segment defined between said upper and lower segments.

13. The support according to claim 12, wherein said spring clips attach said first and second lower segments to said upper posterior segment.

14. The support according to claim 1, wherein said upper segment defines upper anterior segments.

15. The support according to claim 1, wherein said upper anterior segments of said upper segment meet to define said inguinal portion.

16. The support for a prosthetic device of claim 1 wherein said at least two bead members are adjustable to increase or decrease the size of said iguinal portion.

17. A support for a prosthesis device comprising:

a harness made of an elastic tubing configured to fit around a body using a plurality of beads and clamps, said tubing configured to form an upper support segment which meets in coincidental alignment along a portion of said tubing by said plurality of beads to form an inguinal portion first and second lower segments extend downwardly from said inguinal portion such that the ends thereof are attached to said support segment by said clamps, wherein said inguinal portion is adapted to securely support the prosthesis device between said plurality of beads and said tubing.

18. The support according to claim 17, wherein said elastic tubing is configured to fit around the lower body of a person.

19. The support according to claim 17, wherein movement of one of said plurality of beads permits adjustment of said harness around the body.

20. The support according to claim 17, wherein movement of one of said plurality of beads causes adjustment of said upper segment.

21. The support according to claim 17, wherein movement of another of said plurality of beads causes adjustment of said first and second lower segments.

22. A support for a prosthesis device comprising:

an elastic member with two end portions configured to surround the waist of the user and further extend around the upper portion of the user's legs and buttocks region;

at least one clamp that attaches said two end portions to said elastic member, and at least two bead members that act to form an iguinal portion from said elastic member which is capable of supporting the prosthetic device.

23. The support for a prosthetic device of claim 22 wherein said at least two bead members are adjustable when attached to said elastic member to increase or decrease the size of said iguinal portion.

24. The support for a prosthetic device of claim 22 wherein said elastic member is an elastic tubing.

25. The support for a prosthetic device of claim 22 wherein said at least one clamp allows adjustment to accommodate waists of varying size.

26. A support for a prosthesis device comprising:

a harness made of an elastic tubing configured to fit around a body using first, second, third and fourth hollow beads and first and second spring clamps, said tubing configured to form first and second lower segments connected to an upper segment adapted to fit around a waist of the body by said first and second spring clamps, respectively, said upper segment meeting in coincidental alignment along one section thereof to define an inguinal portion attached together using said first, second, third and fourth beads, said inguinal portion including a support segment interposed between an upper adjustment segment and a lower adjustment segment, wherein said support segment of said tubing is adapted to securely support one end of the prosthesis device.

* * * * *